(12) United States Patent
Fey et al.

(10) Patent No.: US 11,332,444 B2
(45) Date of Patent: May 17, 2022

(54) METHOD FOR THE HYDROLYSIS OF QUINOLONECARBOXYLIC ESTERS

(71) Applicant: BAYER ANIMAL HEALTH GMBH, Leverkusen (DE)

(72) Inventors: Peter Fey, Wuppertal (DE); Mathias Berwe, Sprockhoevel (DE); Joerg Wirths, Essen (DE); Ralf Wischnat, Bergisch Gladbach (DE); Markus Longerich, Cologne (DE); Antje Dietzel, Essen (DE)

(73) Assignee: Bayer Animal Health GmbH, Leverkusen (DE)

( * ) Notice: Subject to any disclaimer, the term of this patent is extended or adjusted under 35 U.S.C. 154(b) by 0 days.

(21) Appl. No.: 17/049,925

(22) PCT Filed: Apr. 18, 2019

(86) PCT No.: PCT/EP2019/060072
§ 371 (c)(1),
(2) Date: Oct. 22, 2020

(87) PCT Pub. No.: WO2019/206798
PCT Pub. Date: Oct. 31, 2019

(65) Prior Publication Data
US 2021/0078950 A1    Mar. 18, 2021

(30) Foreign Application Priority Data
Apr. 25, 2018 (EP) ..................... 18169170

(51) Int. Cl.
*C07D 215/56* (2006.01)
*C07C 227/18* (2006.01)
*C07C 229/36* (2006.01)

(52) U.S. Cl.
CPC .......... *C07D 215/56* (2013.01); *C07C 227/18* (2013.01); *C07C 229/36* (2013.01)

(58) Field of Classification Search
CPC .................................................. C07D 215/56
See application file for complete search history.

(56) References Cited

U.S. PATENT DOCUMENTS

| | | | |
|---|---|---|---|
| 4,599,334 A | 7/1986 | Petersen et al. | |
| 4,908,366 A | 3/1990 | Schriewer et al. | |
| 5,051,418 A | 9/1991 | Schriewer et al. | |
| 6,133,260 A | 10/2000 | Matzke et al. | |
| 6,278,013 B1 | 8/2001 | Bartel et al. | |
| 6,323,213 B1 | 11/2001 | Bartel et al. | |
| 6,432,948 B1 | 8/2002 | Matzke et al. | |
| 6,590,101 B2 | 7/2003 | Lui et al. | |
| 7,858,120 B2 | 12/2010 | Bosche et al. | |
| 8,231,903 B2 | 7/2012 | Fraatz | |
| 8,545,829 B2 | 10/2013 | Mertin et al. | |
| 8,658,645 B2 | 2/2014 | Daube et al. | |
| 2004/0247560 A1 | 12/2004 | Dirk et al. | |
| 2009/0011045 A1 | 1/2009 | Mertin et al. | |
| 2011/0065719 A1 | 3/2011 | Bosche et al. | |

FOREIGN PATENT DOCUMENTS

| | | |
|---|---|---|
| EP | 0169993 A2 | 2/1986 |
| EP | 0276700 A1 | 8/1988 |
| EP | 1236718 A1 | 9/2002 |
| EP | 1319656 A1 | 6/2003 |
| WO | 97/31001 A1 | 8/1997 |
| WO | 98/26779 A1 | 6/1998 |
| WO | 03/007995 A2 | 1/2003 |
| WO | 03/101422 A2 | 12/2003 |

(Continued)

OTHER PUBLICATIONS

International Search Report of International Patent Application No. PCT/EP2019/060072 dated Jul. 16, 2019.

*Primary Examiner* — Golam M Shameem
(74) *Attorney, Agent, or Firm* — McBee Moore & Vanik IP, LLC; Susan E. Shaw McBee

(57) ABSTRACT

Quinolonecarboxylic esters of the general formula (II) are hydrolyzed to quinolonecarboxylic acids of the general formula (I):

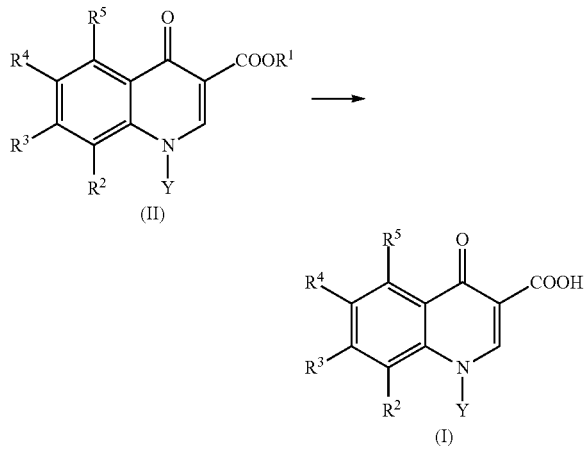

The method comprises the step A):
A) reacting compounds of the formula (II) with a mixture comprising acetic acid, sulfuric acid and water
In step A), ≥30 to ≤40 mol of acetic acid, ≥0.3 to ≤1 mol of sulfuric acid and ≥0.9 to ≤2.5 mol of water are used per mole of compounds of the formula (II). The method is particularly suitable for the synthesis of the intermediate (I) in the synthesis of pradofloxacin.

9 Claims, 1 Drawing Sheet

(56) References Cited

FOREIGN PATENT DOCUMENTS

| WO | 2004014893 A2 | 2/2004 |
|----|---------------|--------|
| WO | 2004/082658 A1 | 9/2004 |
| WO | 2005/018641 A2 | 3/2005 |
| WO | 2005/044271 A1 | 5/2005 |
| WO | 2006/061156 A2 | 6/2006 |

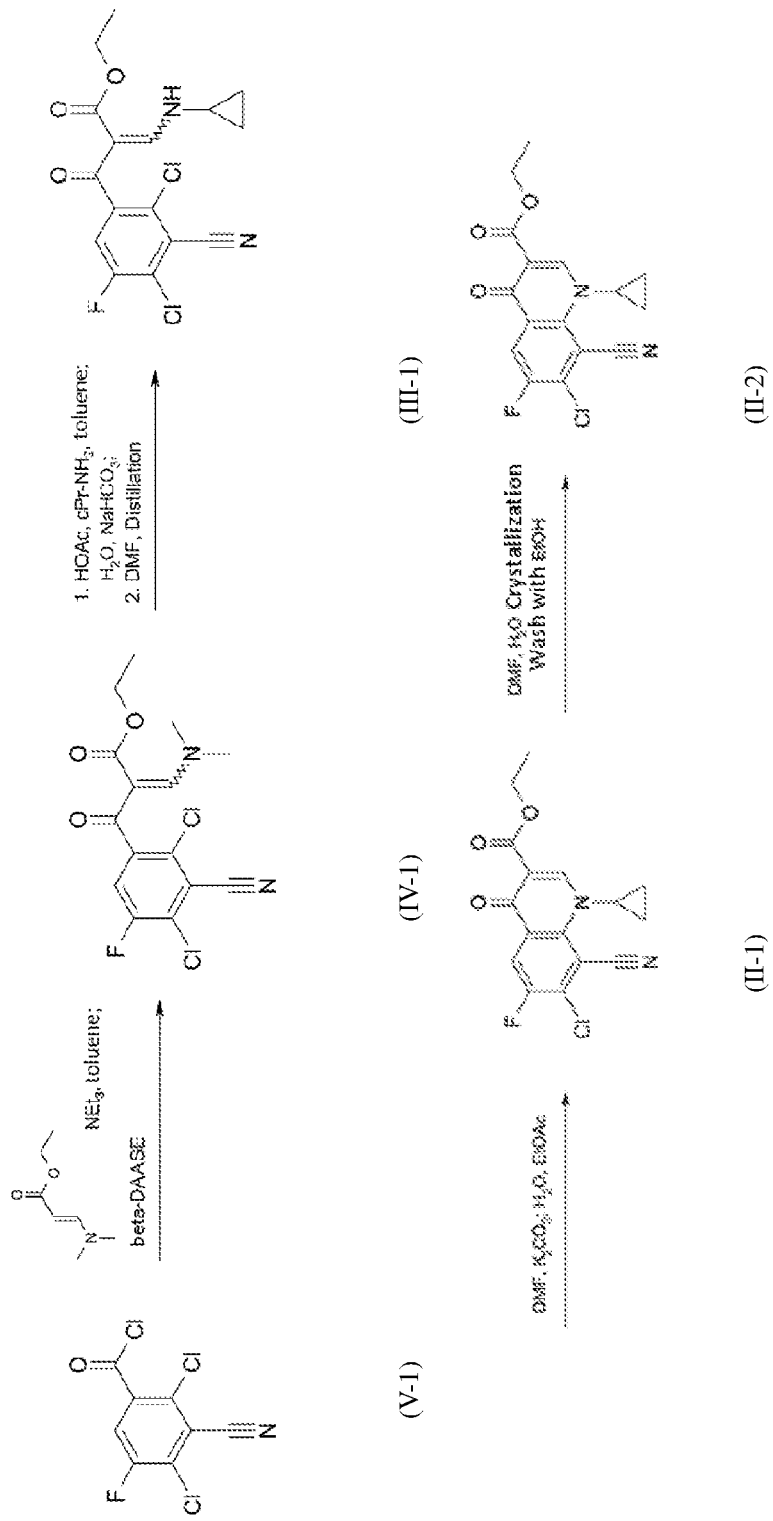

METHOD FOR THE HYDROLYSIS OF QUINOLONECARBOXYLIC ESTERS

CROSS-REFERENCE TO RELATED APPLICATIONS

This application is a National Stage entry of International Application No. PCT/EP2019/060072, filed Apr. 18, 2019, which claims priority to European Patent Application No. 18169170.0, filed Apr. 25, 2018.

BACKGROUND

Field

The present invention relates to a method for the hydrolysis of quinolonecarboxylic esters to quinolonecarboxylic acids. Fluoroquinolonecarboxylic acids are important intermediates for the preparation of known pharmaceutically active compounds from the class consisting of the quinolones. Specific examples include: benofloxacin, binfloxacin, cinoxacin, ciprofloxacin, danofloxacin, difloxacin, enoxacin, enrofloxacin, fleroxacin, ibafloxacin, levofloxacin, lomefloxacin, marbofloxacin, moxifloxacin, norfloxacin, ofloxacin, orbifloxacin, pefloxacin, pipemidic acid, temafloxacin, tosufloxacin, sarafloxacin, sparfloxacin and pradofloxacin.

Description of Related Art

Pradofloxacin is a highly effective quinolone antibiotic in veterinary medicine. Its antibacterial action and indications, application forms and suitable preparations are, for example, in WO 97/31001 A1, WO 03/007995 A1, WO 03/101422 A1, WO 04/082658 A1, WO 05/018641 A1, WO 05/044271 A1 and WO 06/061156 A1.

One step in the multi-stage synthesis of pradofloxacin is the hydrolysis of an ethyl quinolonecarboxylate. For the hydrolysis of quinolonecarboxylic esters, the pH can be lowered by hydrochloric acid or sulfuric acid/acetic acid. The hydrochloric acid method has the disadvantage that the reaction mixture is very corrosive and the equipment provided for carrying out the reaction must accordingly be corrosion-proof. High costs are a consequence of this. Furthermore, the mother liquors must be neutralized prior to disposal at some cost, large amounts of waste arise and the process has a comparatively high number of steps.

The sulfuric acid/acetic acid method has the advantage that the acetic acid used can be recovered by distillation and that less corrosive media can be used.

WO 98/26779 A1 discloses, in example Z 22 of the description, the synthesis of 7-chloro-8-cyano-1-cyclopropyl-6-fluoro-1,4-dihydro-4-oxo-3-quinolinecarboxylic acid. For this purpose, 3.8 g (0.1 mol) of ethyl 7-chloro-8-cyano-1-cyclopropyl-6-fluoro-1,4-dihydro-4-oxo-3-quinolinecarboxylate were heated under reflux in a mixture of 100 ml of acetic acid, 20 ml of water and 10 ml of concentrated sulfuric acid for 3 hours. After cooling, the mixture was poured onto 100 ml of ice water, the precipitated precipitate was filtered off with suction, washed with water and ethanol and dried at 60° C. under vacuum. 17.3 mol of acetic acid, 1.86 mol of sulfuric acid and 11 mol of water were used per mole of ester.

EP 0 276 700 A1 discloses in example 1 of the description the hydrolysis of ethyl 7-chloro-8-cyano-1-cyclopropyl-6-fluoro-1,4-dihydro-4-oxo-3-quinolinecarboxylate. 1 g of this compound was heated together with 3.5 ml of acetic acid, 3 ml of water and 0.3 ml of sulfuric acid to 140-145° C. for 4 hours. Subsequently, the mixture was diluted with water and the solid isolated. 0.7 g of the free carboxylic acid were obtained with a melting point of 281-282° C. 20 mol of acetic acid, 1.89 mol of sulfuric acid and 55.8 mol of water were used per mole of ester.

EP 0 169 993 A2 discloses in example A of the description that a mixture of 94 g of ethyl 1-cyclopropyl-6,7,8-trifluoro-1,4-dihydro-4-oxo-3-quinolinecarboxylate, 600 ml of glacial acetic acid, 450 ml of water and 70 ml of concentrated sulfuric acid was heated at reflux for 1.5 hours. The hot suspension was then poured onto ice, the precipitate was filtered off under suction, washed with water and dried under vacuum at 100° C. In this manner, 88.9 g of 1-cyclopropyl-6,7,8-trifluoro-1,4-dihydro-4-oxo-3-quinolinecarboxylic acid were obtained. 34.7 mol of acetic acid, 4.35 mol of sulfuric acid and 82.8 mol of water were used per mole of ester.

EP 1 319 656 A1 discloses in example 2 the reaction of 29.4 g of ethyl 1-cyclopropyl-7-chloro-6-fluoro-8-methoxy-1,4-dihydro-4-oxo-3-quinolinecarboxylate (0.088 mol), 160 ml of acetic acid, 100 ml of water and 18 ml of concentrated sulfuric acid. The mixture was stirred at 100-110° C. for 40 minutes. The resulting mixture was cooled and filtered. The precipitate was recrystallized from chloroform-ethanol. This gave 23.8 g of the free carboxylic acid. 31.8 mol of acetic acid, 3.84 mol of sulfuric acid and 61.1 mol of water were used per mole of ester.

EP 1 236 718 A1 discloses in example 1 that 300 g of ethyl 1-cyclopropyl-6,7,8-trifluoro-1,4-dihydro-4-oxo-3-quinolinecarboxylate, 106.8 g of water and 426 g of acetic acid were initially charged and 3.8 g of sulfuric acid were added. The mixture was heated to reflux for 3 hours. 310 ml of distillate were then distilled off until a bottom temperature of 109° C. was reached. The mixture was then cooled to 80° C. and 157.5 g of 4.8% by weight sodium acetate solution were added dropwise. The pH was then in the range of 3 to 4. The mixture was then cooled to 20° C. and the solid was filtered off with suction. The solid was washed with 200 ml of water and dried under reduced pressure at 50° C. 270.3 g of 1-cyclopropyl-6,7,8-trifluoro-1,4-dihydro-4-oxo-3-quinolinecarboxylic acid were isolated, which corresponds to a yield of 99% of theory. 7.4 mol of acetic acid, 0.04 mol of sulfuric acid and 6.2 mol of water were used per mole of ester.

SUMMARY

The object of the present invention was to provide an improved method for the hydrolysis of quinolonecarboxylic esters in which the formation of waste products to be processed is as low as possible and in which the resulting quinolonecarboxylic acid has the highest possible purity.

The object is achieved in accordance with the invention by a method for the hydrolysis of quinolonecarboxylic esters of the general formula (II) to obtain quinolonecarboxylic acids of the general formula (I):

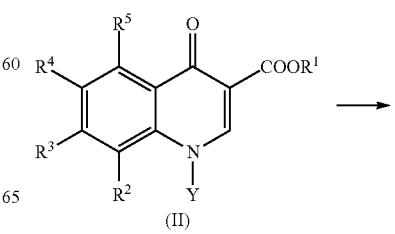

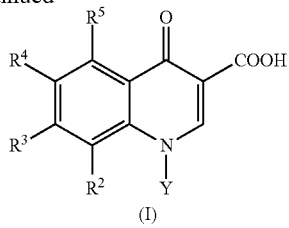

(I)

wherein in formula (II) $R^1$ is $C_1$-$C_4$-alkyl and
concordantly in formulae (I) and (II):
$R^2$ is hydrogen, $C_1$-$C_4$-alkyl, $C_1$-$C_4$-alkoxy, halogen, nitro or cyano,
$R^3$ and $R^4$ are each a halogen,
$R^5$ is hydrogen, $C_1$-$C_4$-alkyl, halogen or nitro, and
Y is $C_1$-$C_6$-alkyl, cyclopropyl or phenyl, each of which can optionally be substituted by halogen,
wherein $R^2$ and Y together can also be a —$CH_2$—$CH_2$—O— or —$CH(CH_3)$—$CH_2$—O— bridge bonded to the nitrogen atom by a carbon atom and
wherein at least one of the radicals $R^2$ to $R^5$ is fluorine, comprising the step of:
A) reacting compounds of the formula (II) with a mixture comprising acetic acid, sulfuric acid and water.

In step A), ≥30 to ≤40 mol of acetic acid, ≥0.3 to ≤1 mol of sulfuric acid and ≥0.9 to ≤2.5 mol of water are used per mole of compounds of the formula (II). Preference is given to using ≥32 to ≤38 mol of acetic acid, ≥0.4 to ≤0.8 mol of sulfuric acid and ≥0.9 to ≤2.3 mol of water, more preferably ≥33 to ≤35 mol of acetic acid, ≥0.4 to ≤0.6 mol of sulfuric acid and ≥0.9 to ≤2.2 mol of water per mole of compounds of the formula (II).

DETAILED DESCRIPTION OF A PREFERRED EMBODIMENT

In the method according to the invention, acetic acid and sulfuric acid can be used in water-containing or anhydrous form. The quantitative data described relate to 100% acetic acid and 100% sulfuric acid. If water-containing acetic acid and/or water-containing sulfuric acid is used, less water must be used according to their water content. Acetic acid is preferably used in the form of glacial acetic acid, sulfuric acid preferably in the form of 96 to 100% sulfuric acid.

The addition of water, acetic acid and sulfuric acid is preferably carried out such that the ester (II), the acetic acid and the sulfuric acid are initially charged and the water is then added. It is also possible to firstly initially charge the ester (II), the water and the acetic acid and then to add the sulfuric acid. The reaction mixture is preferably heated for 10 to 25 hours, more preferably 12 to 22, particularly preferably 16 to 20 hours.

In step A), preferably no further chemically reactive or catalytically active compounds are used besides the ester (II), acetic acid, water and sulfuric acid.

Preferred embodiments of the method according to the invention are described below. They may be combined with one another as desired unless the opposite is clear from the context.

In one embodiment of the method in step A), ≥95 mol % of the compounds of the formula (II) used are converted to compounds of the formula (I). This yield is preferably ≥96 mol % and more preferably ≥99.5 mol %.

In a further embodiment of the method, the reaction in step A) is conducted at a temperature of ≥90° C. to ≤99° C.

This temperature is preferably ≥92 to ≤97° C., more preferably ≥94 to ≤95° C. It has been found that higher reaction temperatures in this step results in an increased content of impurities (cf. the analytical data stated further below for examples and comparative examples).

The heating of the reaction mixture can be carried out at reduced pressure, atmospheric pressure or elevated pressure. For example, pressures in the range from 0.5 to 3 bar are possible. Unless stated otherwise, all method steps described here are typically operated at atmospheric pressure.

One advantage of the method according to the invention is that no distillation is required and that the product can be isolated directly from the reaction mixture by filtration. This is more cost-effective than the comparative methods with a distillation step.

The quinolonecarboxylic acid produced can be isolated from the mixture present for example such that the precipitate present is then filtered under suction, washed and dried. Ethanol is preferably used to wash the precipitate, particularly preferably the precipitate is firstly washed with acetic acid and then with ethanol. Washing with water can be avoided, whereby the acetic acid collected may also be more easily recovered. It is advantageous to wash the isolated product repeatedly in order to obtain it sufficiently free and largely without adhering sulfuric acid. Addition of base at this point in the method according to the invention is not required. This again also saves wastes and costs.

In a further embodiment of the method, concordantly in formulae (I) and (II) it holds that:
$R^2$ is hydrogen, methyl, methoxy, fluorine, chlorine, nitro or cyano,
$R^3$ is fluorine or chlorine,
$R^4$ is fluorine,
$R^5$ is hydrogen, methyl, fluorine, chlorine or nitro,
Y is methyl, ethyl, isopropyl, cyclopropyl, fluorocyclopropyl, 4-fluorophenyl or 2,4-difluorophenyl
and in formula (I) $R^1$ is methyl or ethyl.

It is also possible that concordantly in formulae (I) and (II):
$R^2$ is hydrogen, $C_1$-$C_4$-alkoxy or cyano,
$R^3$ is halogen, especially chlorine,
$R^4$ is fluorine,
$R^5$ is hydrogen,
Y is cyclopropyl
and in formula (I) $R^1$ is methyl or ethyl.

In a further embodiment of the method, formula (I) is 1-cyclopropyl-6,7,8-trifluoro-1,4-dihydro-4-oxo-3-quinolinecarboxylic acid, 1-cyclopropyl-6,7-difluoro-1,4-dihydro-4-oxo-3-quinolinecarboxylic acid, 1-cyclopropyl-6,7-difluoro-8-cyano-1,4-dihydro-4-oxo-3-quinolinecarboxylic acid, 1-(2-fluoro)cyclopropyl-6,7-difluoro-1,4-dihydro-4-oxo-3-quinolinecarboxylic acid, 1-cyclopropyl-8-chloro-6,7-difluoro-1,4-dihydro-4-oxo-3-quinolinecarboxylic acid, 1-ethyl-6,7,8-trifluoro-1,4-dihydro-4-oxo-3-quinolinecarboxylic acid or 1-cyclopropyl-6-fluoro-7-chloro-8-cyano-1,4-dihydro-4-oxo-3-quinolinecarboxylic acid.

In a further embodiment of the method, formulae (II) and (I) have the following definitions according to formulae (II-1) and (I-1) respectively:

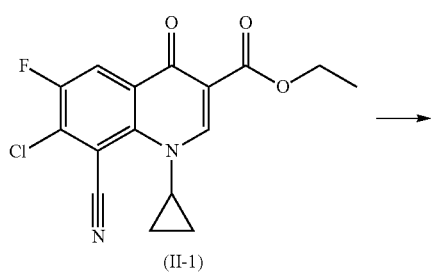

(II-1)

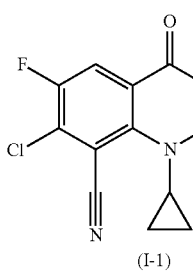

(I-1)

In a further embodiment of the method, the compounds of the formula (II) are obtainable by reacting compounds of the general formula (III):

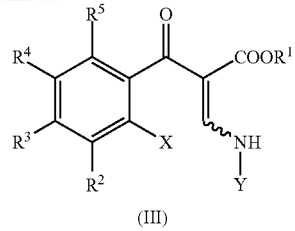

(III)

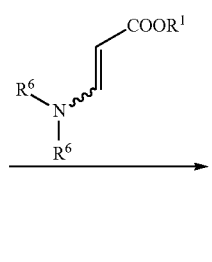

(II)

wherein $R^1$ to $R^5$ and Y have the aforementioned definitions and X is halogen.

In a further embodiment of the method, the compounds of the formula (III) are obtainable by reacting compounds of the general formula (IV):

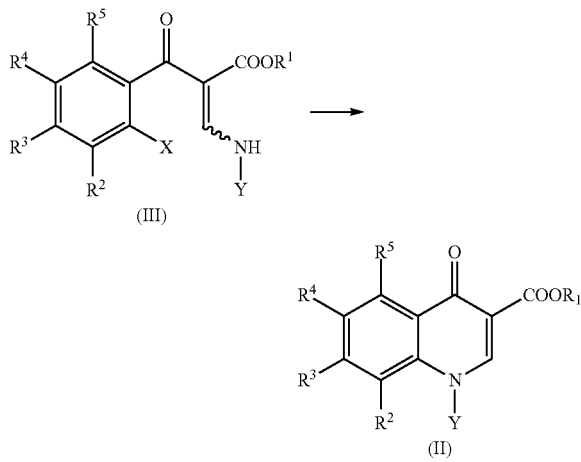

(IV)

and wherein $R^1$ to $R^5$, X and Y have the aforementioned definitions and $R^6$ is $C_1$-$C_4$-alkyl.

In a further embodiment of the method, the compounds of the formula (IV) are obtainable by reacting compounds of the general formula (V):

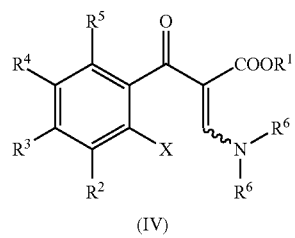

(V)

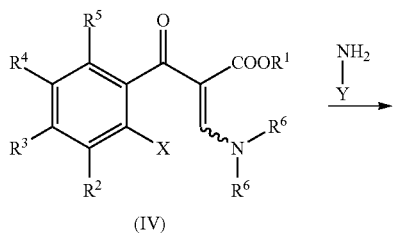

(IV)

and wherein $R^1$ to $R^6$, X and Y have the aforementioned definitions and X' is halogen.

For the preferred preparation of the pradofloxacin intermediate (I), it would be the case in the reaction sequence:
(V)→(IV)→(III)→(II)→(I)
that in all relevant compounds of these general formulae, $R^1$ is ethyl, $R^2$ is cyano, $R^3$ is chlorine, $R^4$ is fluorine, $R^5$ is hydrogen, $R^6$ is methyl, X is chlorine, X' is chlorine and Y is cyclopropyl.

EXAMPLES

The present invention is elucidated in detail by the examples which follow, but without being limited thereto. A synthetic scheme is shown in FIG. 1.

Example 1

Synthesis of ethyl 7-chloro-8-cyano-1-cyclopropyl-6-fluoro-4-oxo-1,4-dihydroquinoline-3-carboxylate (formula (II-2) in FIG. 1)

To 11.8 kg of toluene were added 2.70 kg (18.8 mol) of ethyl (2E)-3-(dimethylamino)acrylate (beta-dimethylamino-acrylate, β-DAASE) and 2.12 kg (20.9 mol) of triethylamine heated at Ti=45° C. to 55° C. A solution of 4.50 kg (17.8 mol) of 2,4-dichloro-3-cyano-5-fluorobenzoyl chloride (formula (V-1) in FIG. 1) in 11.6 kg of toluene was then metered in at Ti=50° C. The reaction mixture was stirred at Ti=50°

C. for 3 hours and cooled to Ti=22° C. The suspension was filtered and the filter cake was washed with 3.4 kg of toluene. To the filtrate (formula (IV-1) in FIG. 1) were metered in 1.23 kg (20.5 mol) of acetic acid and a solution of 1.11 kg (19.4 mol) of cyclopropylamine in 2.40 kg of toluene over 2 hours at Ti=5-15° C. and the mixture was further stirred for 5 hours at Ti=10° C. 13.5 kg of water were then added, the mixture was heated at Ti=40° C. and stirring was continued at this temperature for 30 minutes. The phases were then separated at Ti=40° C. A solution of 300 g of sodium carbonate in 6.0 kg of water was added to the organic phase, the mixture was heated to Ti=40° C., further stirred for 30 minutes and the phases separated at Ti=40° C.

An amount of 22.6 L was distilled off from the organic phase under reduced pressure up to a jacket temperature of 60° C. 19.2 kg of N,N-dimethylformamide were then added and the mixture was stirred for at least 10 minutes at 40° C. Subsequently, the mixture was again distilled under reduced pressure up to a jacket temperature of Tm=60° C. until no more distillate passed over and the residue (formula (III-1) in FIG. 1) was cooled to room temperature.

To the residue were added 2.22 kg (16.0 mol) of potash, the suspension was heated to Ti=55° C. and the mixture was stirred at this temperature for 5 h. The mixture was cooled to Ti=22° C. and an amount of distillate of 16.5 l was distilled off under reduced pressure up to a jacket temperature of 80° C. To the residue were added 18.0 kg of water and the mixture was then stirred at Ti=55° C. for at least 10 minutes. The mixture was then cooled over 2 hours to Ti=5° C. and further stirred at this temperature for 2 hours.

The resulting product was filtered off, washed twice with 6.0 kg of water each time and stirred with 9.9 kg of ethyl acetate for at least 3 hours at Ti=22° C. The suspension was filtered and the filter cake washed twice with 4.8 kg of ethyl acetate each time and the crude product (formula (II-1) in FIG. 1) was dried at 50° C. under reduced pressure for at least 12 hours.

Yield: 5.08 kg; 85.1% of theory based on 2,4-dichloro-3-cyano-5-fluorobenzoyl chloride.

2.96 kg of crude product were heated in 29.4 kg of N,N-dimethylformamide at 60° C. and insoluble impurities were filtered off at this temperature. 3.8 kg of water were added to the filtrate which was then stirred for 1.5 hours and then 13.9 kg of water were metered in over 1.5 hours. The resulting suspension was cooled to Ti=22° C., stirred for 30 minutes and the solid filtered off. The Nutsch filtercake was washed with 3.1 kg of water, then twice with 2.8 kg of ethanol each time, and dried at 50° C. under reduced pressure for at least 12 hours (formula (II-2) in FIG. 1). The method described here has the advantage that an ester (II-2) can be prepared in high purity. This is favorable for preparing the free quinolonecarboxylic acids in high purity. (The ester of the formula (II-2) is produced by a purification step from the ester of the formula (II-1). Both formulae therefore describe the same chemical structure. The different designation of the formulae is only intended to illustrate the different degree of purity)

Yield: 2.87 kg; ca. 97% of theory based on crude product

Example 2

Hydrolysis of the Product of Example 1

To 20.0 g (59.8 mmol) of the product from example 1 (formula (II-2) in FIG. 1) were added 122.8 g (2.04 mol) of acetic acid, 3.37 g (33.0 mmol) of sulfuric acid and 1.1 g (63.0 mmol) of water. The mixture was heated to 95° C. and stirred at this temperature for 18.5 h. The suspension was cooled to 10° C., the solid filtered off with suction, washed with 48 ml of acetic acid and then with 48 ml of ethanol and dried overnight at 60° C. in the vacuum drying cabinet.

Per mole of (II-2) were used: 34.11 mol of acetic acid, 0.55 mol of sulfuric acid and 1.05 mol of water.

Yield: 17.6 g; (96.1% of theory)

For the purity, see the table further below.

Example 3

Hydrolysis of the Product of Example 1

To 20.0 g (59.8 mmol) of the product from example 1 (formula (II-2) in FIG. 1) were added 122.8 g (2.04 mol) of acetic acid, 3.37 g (33.0 mmol) of sulfuric acid and 2.3 g (126.0 mmol) of water. The mixture was heated to 95° C. and stirred at this temperature for 18.5 h. The suspension was cooled to 10° C., the solid filtered off with suction, washed with 48 ml of acetic acid and then with 48 ml of ethanol and dried overnight at 60° C. in the vacuum drying cabinet.

Per mole of (II-2) were used: 34.11 mol of acetic acid, 0.55 mol of sulfuric acid and 2.10 mol of water.

Yield: 17.8 g; (97.1% of theory)

For the purity, see the table further below.

Comparative Example 1

According to the Procedure from Example 1 of EP1236718

To 30.0 g (89.6 mmol) of the product from example 1 (formula (II-2) in FIG. 1) were added 39.6 g (656.1 mmol) of acetic acid, 0.20 ml (3.5 mmol) of sulfuric acid and 9.9 g (549.5 mmol) of water. The mixture was heated under reflux for 3 h. 14.1 g of distillate were then distilled off until a bottom temperature of 109° C. was reached. The mixture was cooled to 80° C. and 40.1 g of 4.8% by weight sodium acetate solution were added dropwise. The pH was then in the range of 3 to 4. The mixture was then cooled to 20° C. and the solid was filtered off with suction. The solid was washed with 50 ml of water and dried under reduced pressure at 50° C.

Per mole of (II-2) were used: 7.32 mol of acetic acid, 0.04 mol of sulfuric acid and 6.13 mol of water.

Yield: 26.7 g; (97.2% of theory)

For the purity, see the table further below.

Comparative Example 2

According to the Procedure of Example 2 of EP 1 236 718

To 30.0 g (89.6 mmol) of the product from example 1 (formula (II-2) in FIG. 1) were added 78.9 g (1.31 mol) of acetic acid, 0.51 ml (9.1 mmol) of sulfuric acid and 2.25 g (124.9 mmol) of water. The mixture was heated under reflux for 4 h. 8.1 g of distillate were then distilled off until a bottom temperature of 109° C. was reached. The mixture was cooled to 80° C. and 75.3 g of 4.8% by weight sodium acetate solution were added dropwise. The pH was then in the range of 3 to 4. The mixture was then cooled to 20° C. and the solid was filtered off with suction. The solid was washed with 50 ml of water and dried under reduced pressure at 50° C.

Per mole of (II-2) were used: 14.62 mol of acetic acid, 0.10 mol of sulfuric acid and 1.39 mol of water.

Yield: 27.0 g; (98.2% of theory)

For the purity, see the table further below.

Comparative Example 3

According to the Procedure from Example Z 22 of WO98/26779

To 9.5 g (28.4 mmol) of the product from example 1 (formula (II-2) in FIG. 1) were added 29.5 g (490.9 mmol) of acetic acid, 5.2 g (52.5 mmol) of sulfuric acid and 5.6 g (310.2 mmol) of water. The mixture was heated under reflux for 3 h and cooled to 20° C. The mixture was then added to 28 g of ice water and the solid was filtered off with suction. The solid was washed with 100 ml of water and 10 ml of ethanol and dried under reduced pressure at 60° C.

Per mole of (II-2) were used: 17.28 mol of acetic acid, 1.85 mol of sulfuric acid and 10.92 mol of water.

Yield: 8.5 g; (97.7% of theory)

The following table summarizes the purities of the hydrolysis products of the formula I-1 obtained in the examples and comparative examples.

| | Example 2 | Example 3 | Comparative 1 | Comparative 2 | Comparative 3 |
|---|---|---|---|---|---|
| Residual content of ethyl ester (II-2)* | 0.196 | 0.268 | 0.772 | 0.436 | 0.108 |
| Total content of unspecified impurities* | 0.005 | 0.007 | 0.124 | 0.130 | 0.146 |
| Assay i.d.s.** | 100.116 | 100.349 | 97.904 | 97.398 | 99.6 |

*data in area percent (determined by HPLC analysis)
**data in percent by weight
i.d.s. signifies "in dried substance"

It is obvious that products are obtained in the method according to the invention with greater purity than in the comparative methods in which the required ratios of reactant (II-2), acetic acid, sulfuric acid and water are not observed.

The invention claimed is:

1. A method for hydrolysis of one or more quinolonecarboxylic esters of formula (II) to obtain one or more quinolonecarboxylic acids of formula (I):

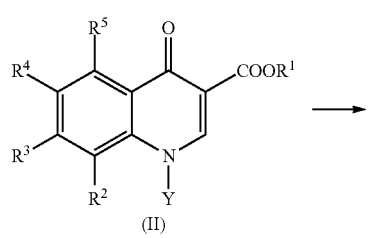

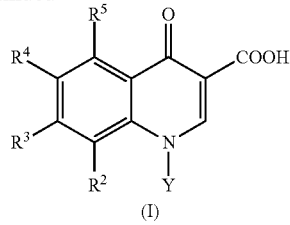

wherein in formula (II) $R^1$ is $C_1$-$C_4$-alkyl and concordantly in formulae (I) and (II):

$R^2$ is hydrogen, $C_1$-$C_4$-alkyl, $C_1$-$C_4$-alkoxy, halogen, nitro or cyano, $R^3$ and $R^4$ are each a halogen, $R^5$ is hydrogen, $C_1$-$C_4$-alkyl, halogen or nitro, and Y is $C_1$-$C_6$-alkyl, cyclopropyl or phenyl, each of which can optionally be substituted by halogen, wherein $R^2$ and Y together can also be a —$CH_2$—$CH_2$—O— or —$CH(CH_3)$—$CH_2$—O— bridge bonded to the nitrogen atom by a carbon atom and wherein at least one of the radicals $R^2$ to $R^5$ is fluorine, comprising:

A) reacting one or more compounds of formula (II) with a mixture comprising acetic acid, sulfuric acid and water wherein in A), ≥30 to ≤40 mol of acetic acid, ≥0.3 to ≤1 mol of sulfuric acid and ≥0.9 to ≤2.5 mol of water are used per mole of compounds of the formula (II).

2. The method according to claim 1, wherein in A)≥95 mol % of the compounds of formula (II) used are converted to one or more compounds of formula (I).

3. The method according to claim 1, wherein the reaction in A) is carried out at a temperature of ≥90 to ≤99° C.

4. The method according to claim 1, wherein concordantly in formulae (I) and (II):

$R^2$ is hydrogen, methyl, methoxy, fluorine, chlorine, nitro or cyano, $R^3$ is fluorine or chlorine, $R^4$ is fluorine, $R^5$ is hydrogen, methyl, fluorine, chlorine or nitro, Y is methyl, ethyl, isopropyl, cyclopropyl, fluorocyclopropyl, 4-fluorophenyl or 2,4-difluorophenyl and in formula (I) $R^1$ is methyl or ethyl.

5. The method according to claim 1, wherein formula (I) is 1-cyclopropyl-6,7,8-trifluoro-1,4-dihydro-4-oxo-3-quinolinecarboxylic acid, 1-cyclopropyl-6,7-difluoro-1,4-dihydro-4-oxo-3-quinolinecarboxylic acid, 1-cyclopropyl-6,7-difluoro-8-cyano-1,4-dihydro-4-oxo-3-quinolinecarboxylic acid, 1-(2-fluoro)cyclopropyl-6,7-difluoro-1,4-dihydro-4-oxo-3-quinolinecarboxylic acid, 1-cyclopropyl-8-chloro-6,7-difluoro-1,4-dihydro-4-oxo-3-quinolinecarboxylic acid, 1-ethyl-6,7,8-trifluoro-1,4-dihydro-4-oxo-3-quinolinecarboxylic acid or 1-cyclopropyl-6-fluoro-7-chloro-8-cyano-1,4-dihydro-4-oxo-3-quinolinecarboxylic acid.

6. The method according to claim 1, wherein formulae (II) and (I) have the following definition according to the formulae (II-1) and (I-1) respectively:

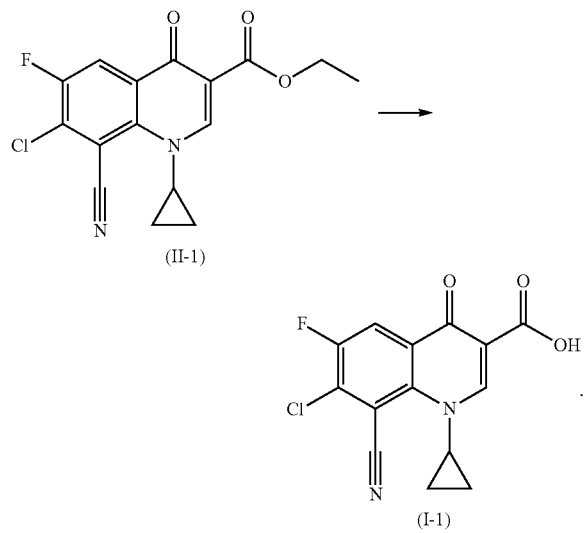

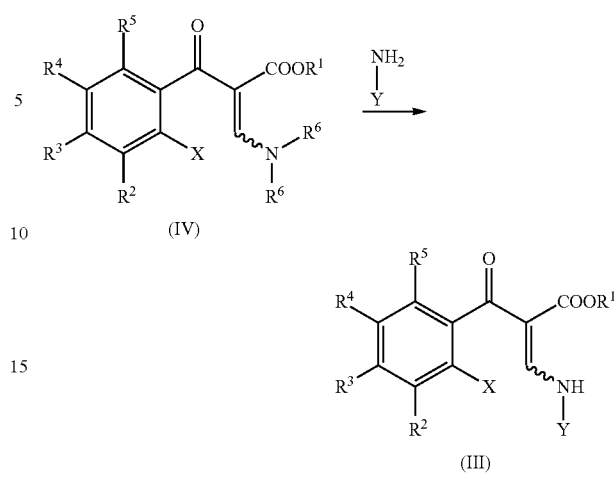

and wherein $R^6$ is $C_1$-$C_4$-alkyl.

9. The method according to claim 8, wherein the one or more compounds of formula (IV) are obtainable by reacting one or more compounds of formula (V):

7. The method according to claim 1, wherein the one or more compounds of formula (II) are obtainable by reacting one or more compounds of formula (III):

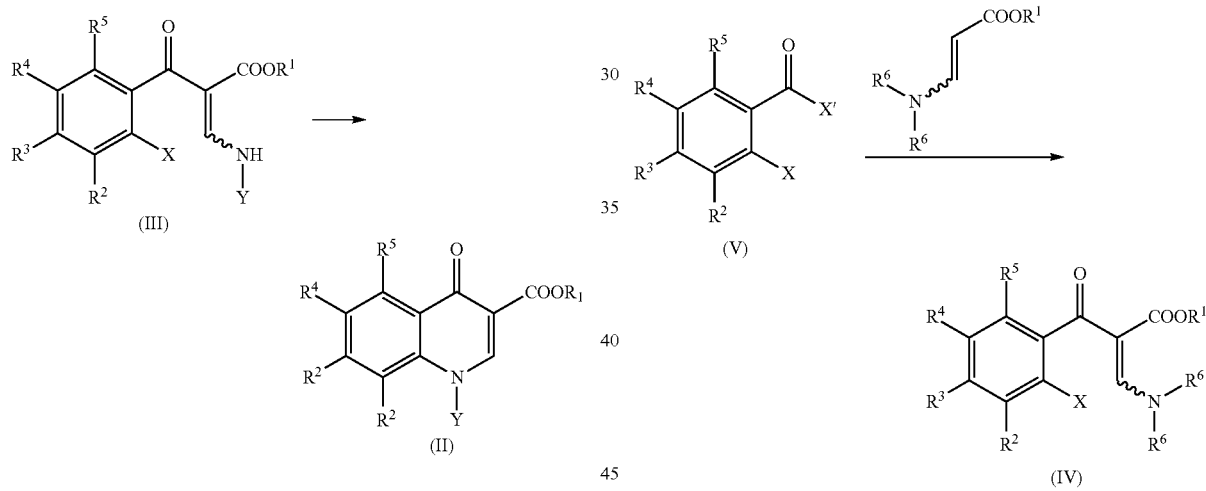

wherein X is halogen.

8. The method according to claim 7, wherein the one or more compounds of formula (III) are obtainable by reacting one or more compounds of formula (IV):

and wherein X' is halogen.

* * * * *